US006460414B1

(12) United States Patent
Erickson et al.

(10) Patent No.: US 6,460,414 B1
(45) Date of Patent: Oct. 8, 2002

(54) AUTOMATED ACOUSTIC MICRO IMAGING SYSTEM AND METHOD

(75) Inventors: Daniel M. Erickson, Schiller Park, IL (US); Daniel W. Micek, Norridge, IL (US); Michael G. Oravecz, Naperville, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 0 days.

(21) Appl. No.: 09/715,359

(22) Filed: Nov. 17, 2000

(51) Int. Cl.[7] .......................... C01N 29/04; F26B 19/00; B65H 1/00
(52) U.S. Cl. .............................. 73/603; 73/633; 34/89; 414/222.01; 414/935
(58) Field of Search .......................... 73/603, 620, 627, 73/633, 590, 596; 209/590, 591; 324/765; 356/237.4; 414/222.01, 935; 34/89

(56) References Cited

U.S. PATENT DOCUMENTS

| | | | | |
|---|---|---|---|---|
| 4,518,992 A | * | 5/1985 | Kessler et al. | 358/112 |
| 4,698,572 A | * | 10/1987 | Stone | 318/568.2 |
| 4,757,716 A | * | 7/1988 | Nottingham et al. | 73/623 |
| 4,991,441 A | * | 2/1991 | Nottinham et al. | 73/633 |
| 5,062,298 A | * | 11/1991 | Falcoff et al. | 73/597 |
| 5,099,693 A | * | 3/1992 | Payne et al. | 73/632 |
| 5,600,068 A | * | 2/1997 | Kessler et al. | 73/620 |
| 5,668,452 A | * | 9/1997 | Villareal et al. | 318/568.16 |
| 5,675,403 A | | 10/1997 | Cerrina et al. | |
| 5,684,252 A | * | 11/1997 | Kessler et al. | 73/618 |
| 5,691,476 A | * | 11/1997 | Madaras | 73/644 |
| 5,896,297 A | * | 4/1999 | Valerino, Sr. | 700/213 |
| 5,915,678 A | | 6/1999 | Slocum et al. | |
| 5,991,005 A | | 11/1999 | Horikawa et al. | |
| 6,005,910 A | | 12/1999 | Chiba et al. | |
| 6,302,534 B1 | * | 3/2000 | Sherwin | 73/628 |
| 6,062,084 A | * | 5/2000 | Chang et al. | 73/601 |
| 6,074,515 A | * | 6/2000 | Iseki et al. | 156/345 |
| 6,164,133 A | * | 12/2000 | Watanabe | 73/432.1 |
| 6,227,946 B1 | * | 5/2001 | Gonzalez-Martin et al. | 451/54 |
| 6,247,368 B1 | * | 6/2001 | Cline et al. | 73/629 |
| 6,357,136 B1 | * | 3/2002 | Erickson et al. | 34/60 |

OTHER PUBLICATIONS

Promotional video of Genmark precision Automated Transport Systems of 310 Caribbean Drive, Sunnyvale CA 94089 shows a vacuum chuck for retaining silicon wafers having elevated hollow posts which retain the wafer.
Wafer handling robots shown in promo literature of PRI Automation; obtained from URL shown on document on Sep. 17, 2000.
Hitachi Wafer Cassette handling Clean Robot promo literature. Appears to show elevated vacuum posts Was obtained from the URL shown on the document on Sep. 17, 2000.
Daihen Corporation promo literature on Wafer Transfer robot; Obtained from URL shown on the document on Sep. 17, 2000.
Modern Optical Engineering, Warren J. Smith, Second Edition, McGraw Hills, pp. 489–490 (1990—4 pages).
The Newport Catalog, Scientific & Laboratory Products, Section 4.2 and 4.3 (1994—5 pages).

* cited by examiner

Primary Examiner—Hezron Williams
Assistant Examiner—Jacques M Saint-Surin
(74) Attorney, Agent, or Firm—Welsh & Katz, Ltd.; John H. Coult

(57) ABSTRACT

An automated acoustic micro imaging system includes a part-storage station favoring a dry environment, a part-transport robot, and a wet-environment inspection station. The wet-environment inspection station has an ultrasonic beam generator, a coupling fluid in which parts are inspected, and a part-retention stage. A moisture barrier is located between the wet-environment inspection station and the part-storage station favoring a dry environment. The inspection station includes a kinematic, quick-change part-retaining chuck and robotic means for interchanging chucks. Automatic acoustic micro imaging methods are disclosed.

76 Claims, 14 Drawing Sheets

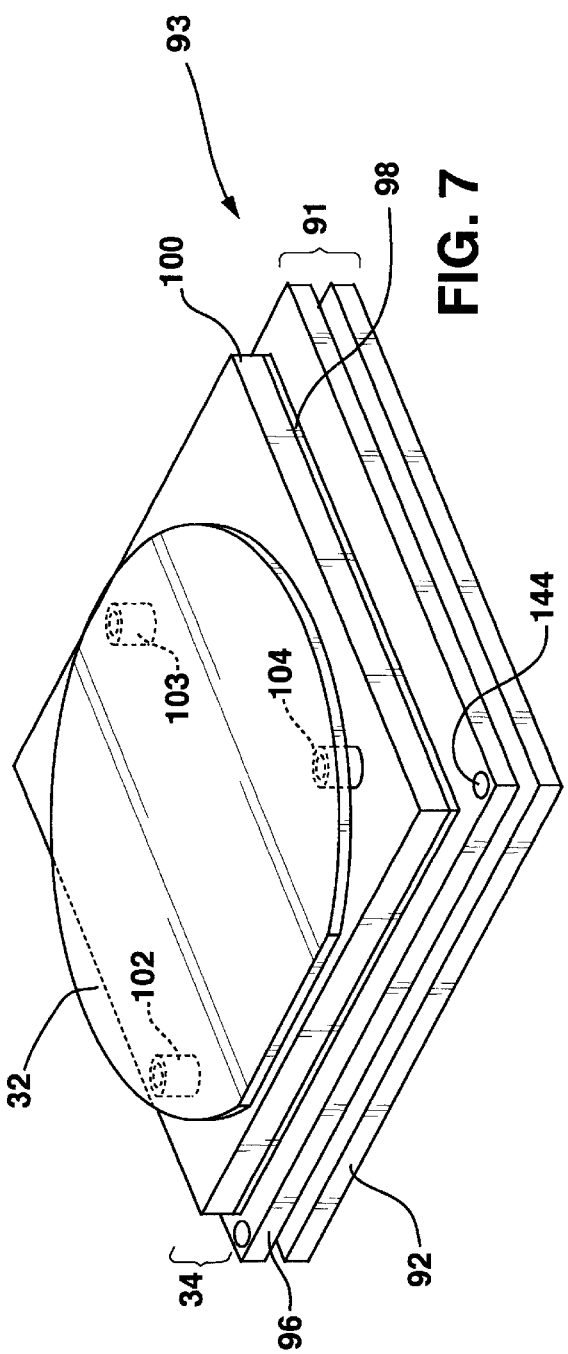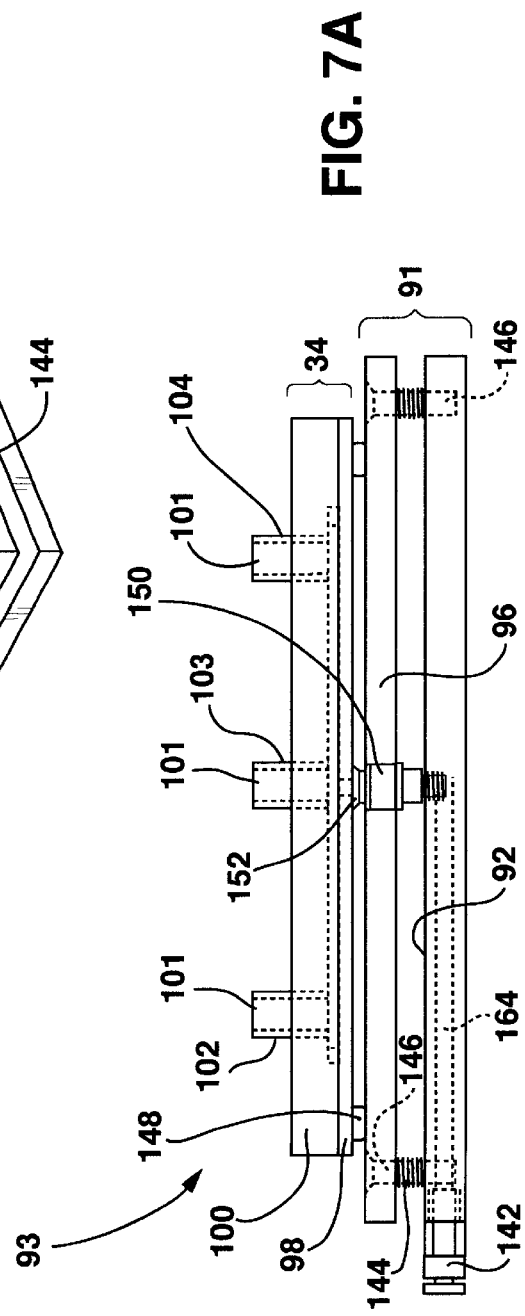

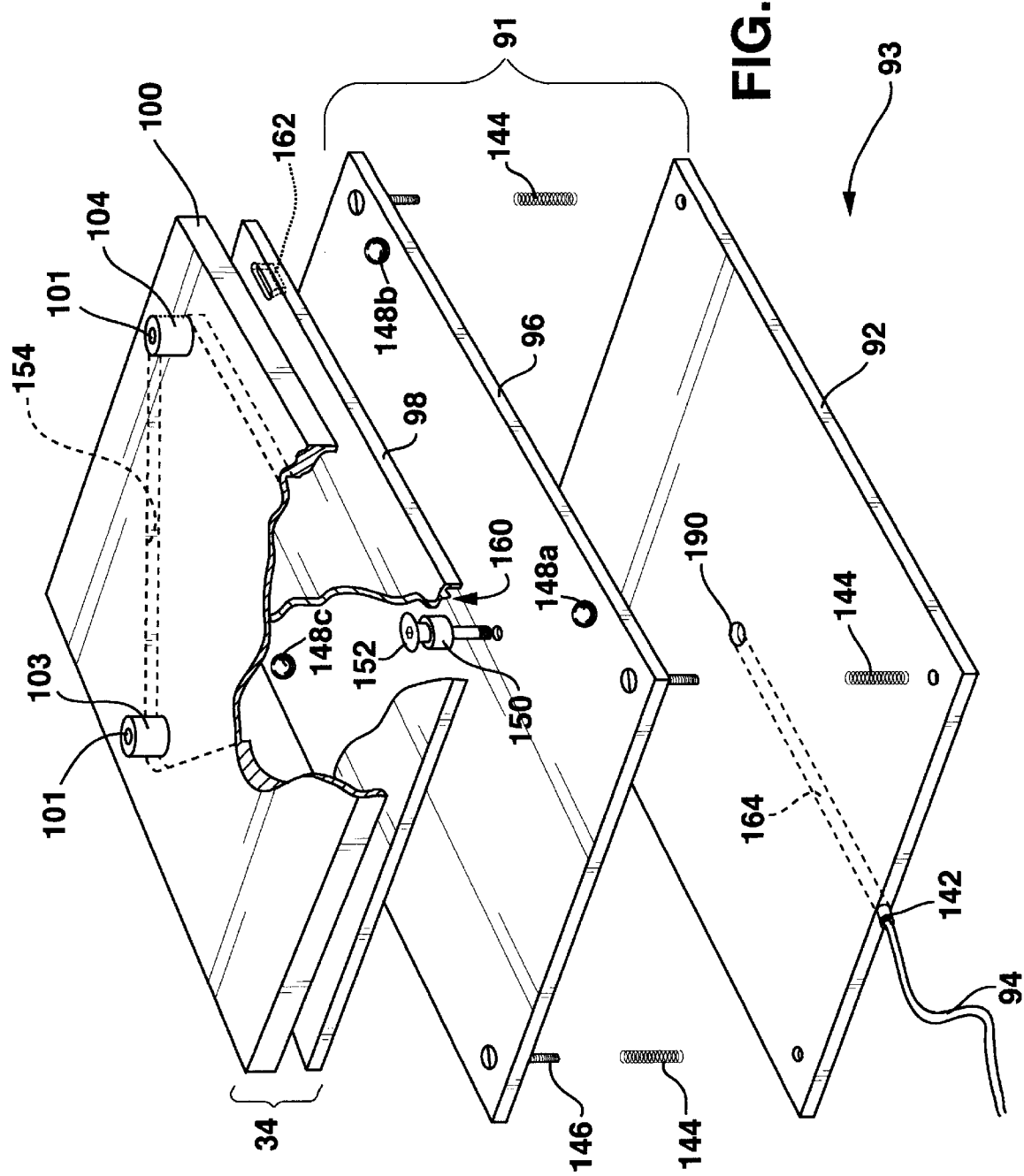

FIG. 9
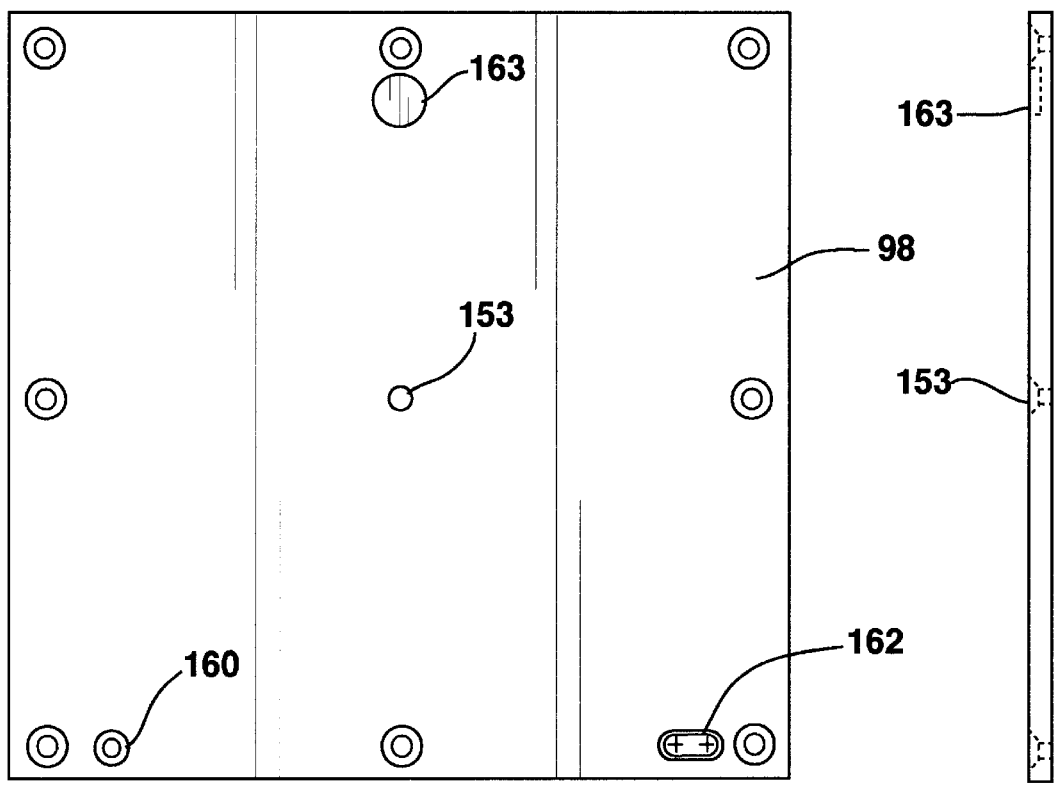
FIG. 9B
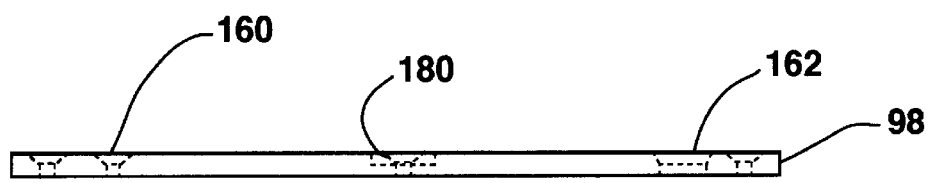
FIG. 9A

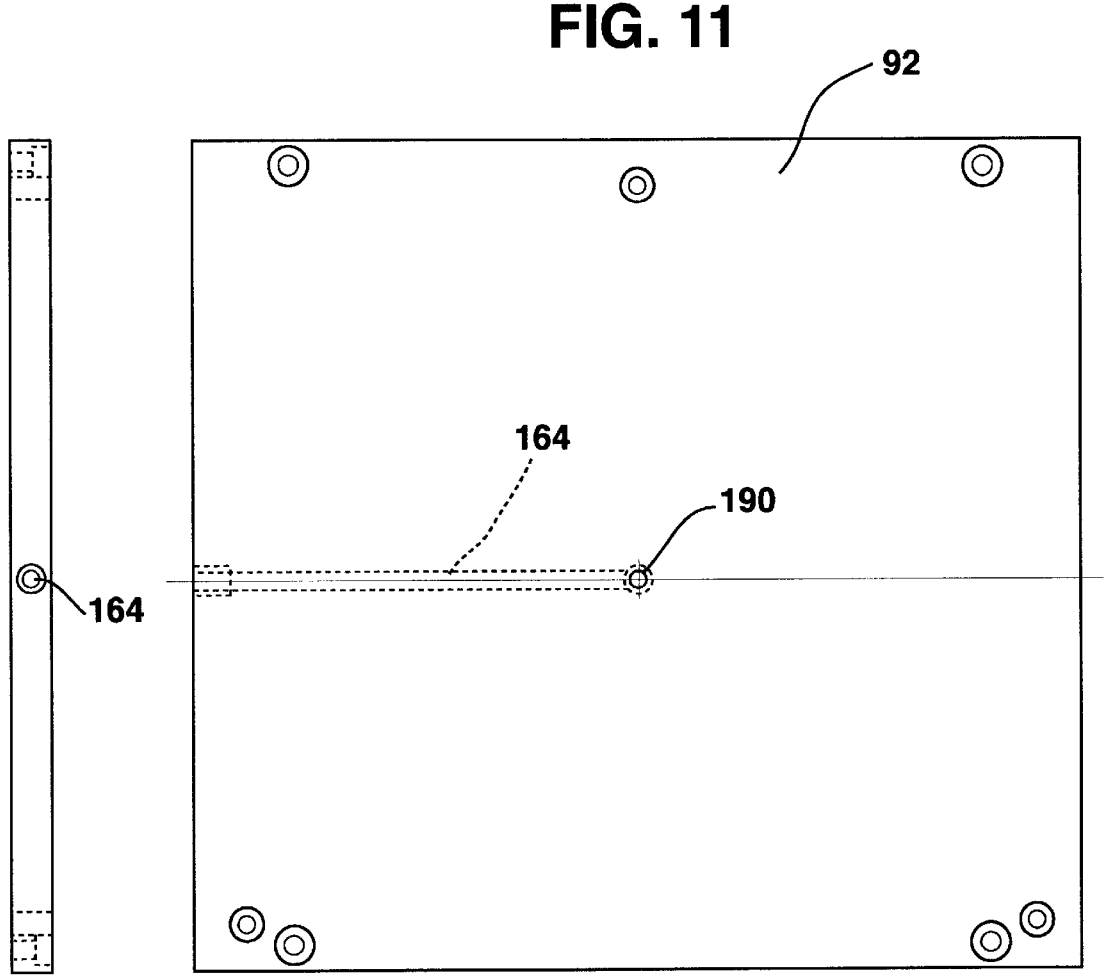
FIG. 11
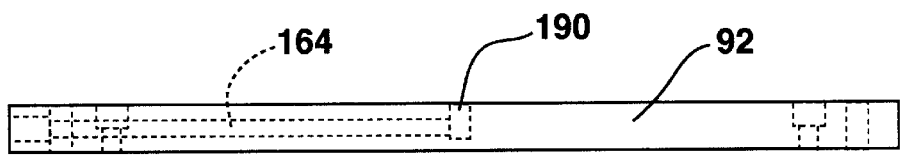
FIG. 11A
FIG. 11B

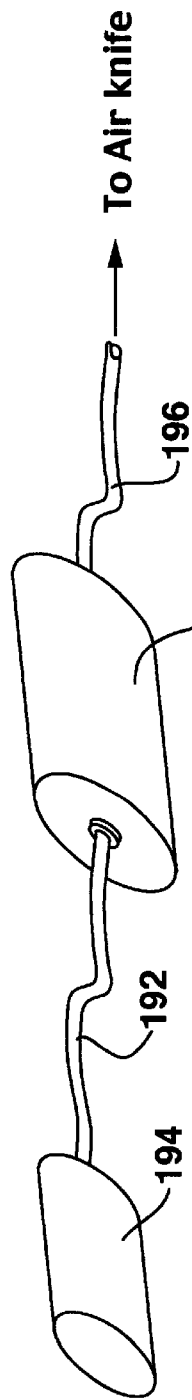
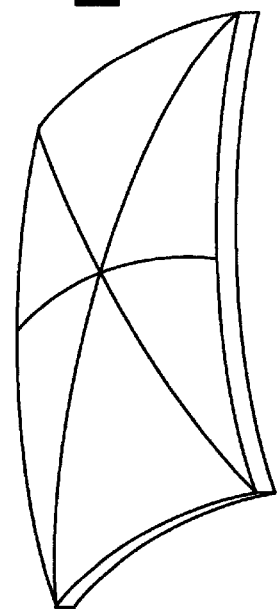
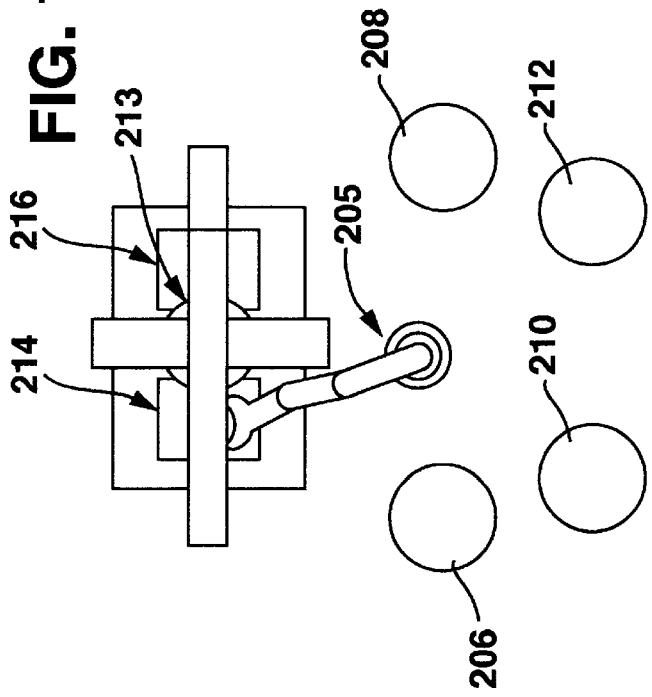
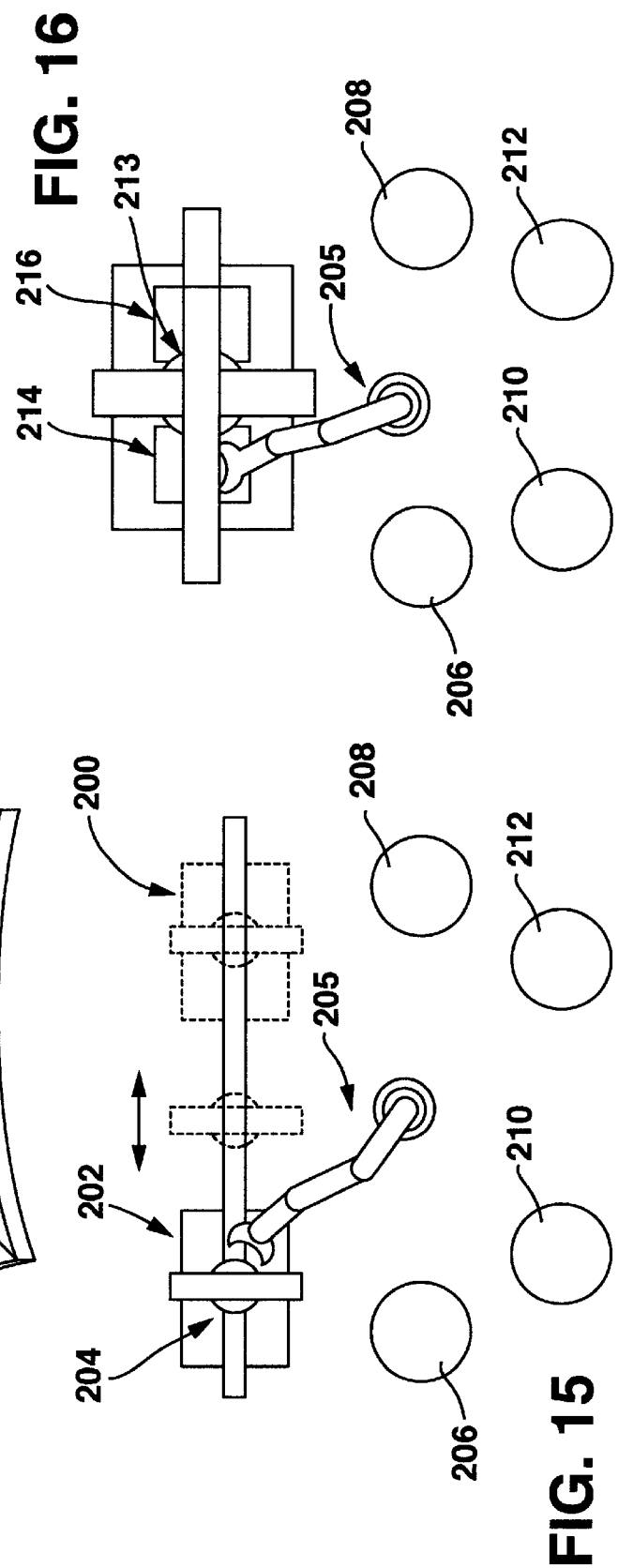
FIG. 13
FIG. 14
FIG. 15
FIG. 16

AUTOMATED ACOUSTIC MICRO IMAGING SYSTEM AND METHOD

BACKGROUND OF THE INVENTION

The present invention is directed to a system and method for automating the inspection of semiconductor wafers and other parts through the use of an acoustic micro imaging system or "AMI" system. An AMI system operated at the high resolutions needed to inspect semiconductor wafers and other parts having microscopic detail requires that the scanning ultrasonic (or "acoustic") beam be coupled to and from the inspected part through water, alcohol or other coupling fluid. The acoustic coupling between the acoustic beam generator, often called a "transducer", and the part is typically accomplished by submerging the beam generator and part in a bath or by creating a gravity or pressure jet or flow between the beam generator and the part through which the acoustic beam travels. The necessitated presence of this coupling fluid creates a very wet scanning environment.

It is common to store wafers in cassettes before and after they are inspected. However, it is important that the wafers after inspection in the wet-environment of the AMI be returned to their storage cassettes in a dry condition—that is, not laden with significant surface moisture. Robots employed to handle wafers commonly employ a vacuum end effector. The wet-environment of an AMI system could be hostile to such commonly available wafer handling robots. Thus the presence of the coupling fluid creates a wet scanning environment that is inimical to automated AMI inspection processes.

Semiconductor wafers typically are circular in shape and are manufactured in a variety of diameters, including 100 mm, 125 mm, 150 mm, and recently 300 mm. During various manufacturing operations, semiconductor wafers are commonly retained by the use of a vacuum chuck having perforated vacuum plate upon which the wafers are situated. Such a vacuum chuck would be rendered inoperative in the wet AMI operating environment.

The processing of different size wafers requires different-sized vacuum chucks which presents yet another obstacle to a fully automated AMI inspection system.

OBJECTS OF THE INVENTION

It is an object of the present invention to provide an AMI system and method for automated inspection of semiconductor wafers and other parts which overcomes the innate incompatibility of commonly employed robotic devices and the hostile wet-environment of an AMI system, and satisfies the need to satisfactorily dry inspected parts before being returned to storage or passed on to another manufacturing process.

It is another object to provide an AMI system which makes possible the automated interchange of part-retention chucks capable of handling parts of different sizes and configurations.

It is a further object to provide for use in an AMI system a part-retention stage in which a vacuum chuck is so constructed as to be capable of quick-change, position-repeatable kinematic mounting without loss of vacuum integrity.

Many other objects will become evident from the following description and claims.

DESCRIPTIONS OF THE FIGURES

Figure 3:
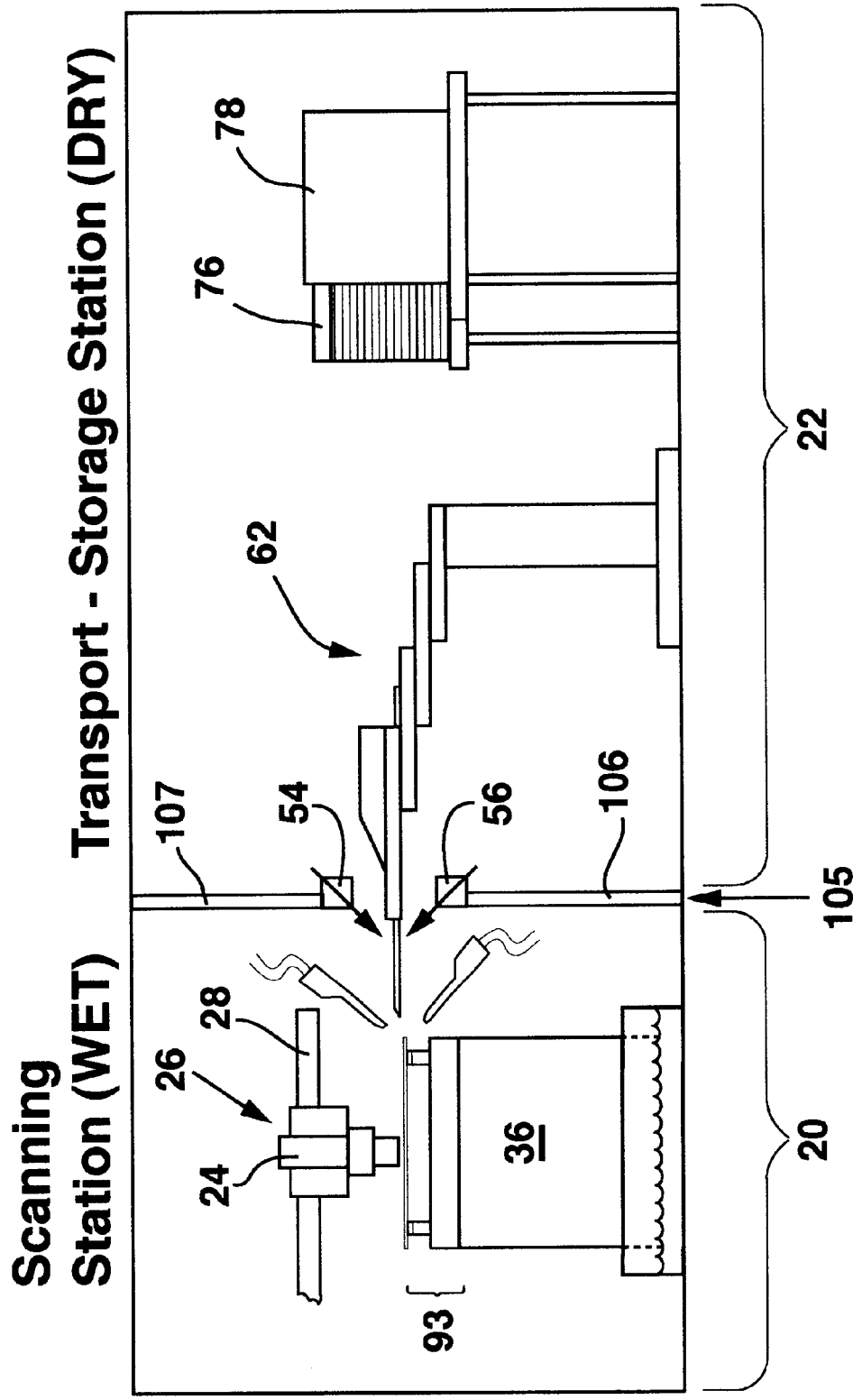
Figure 4:
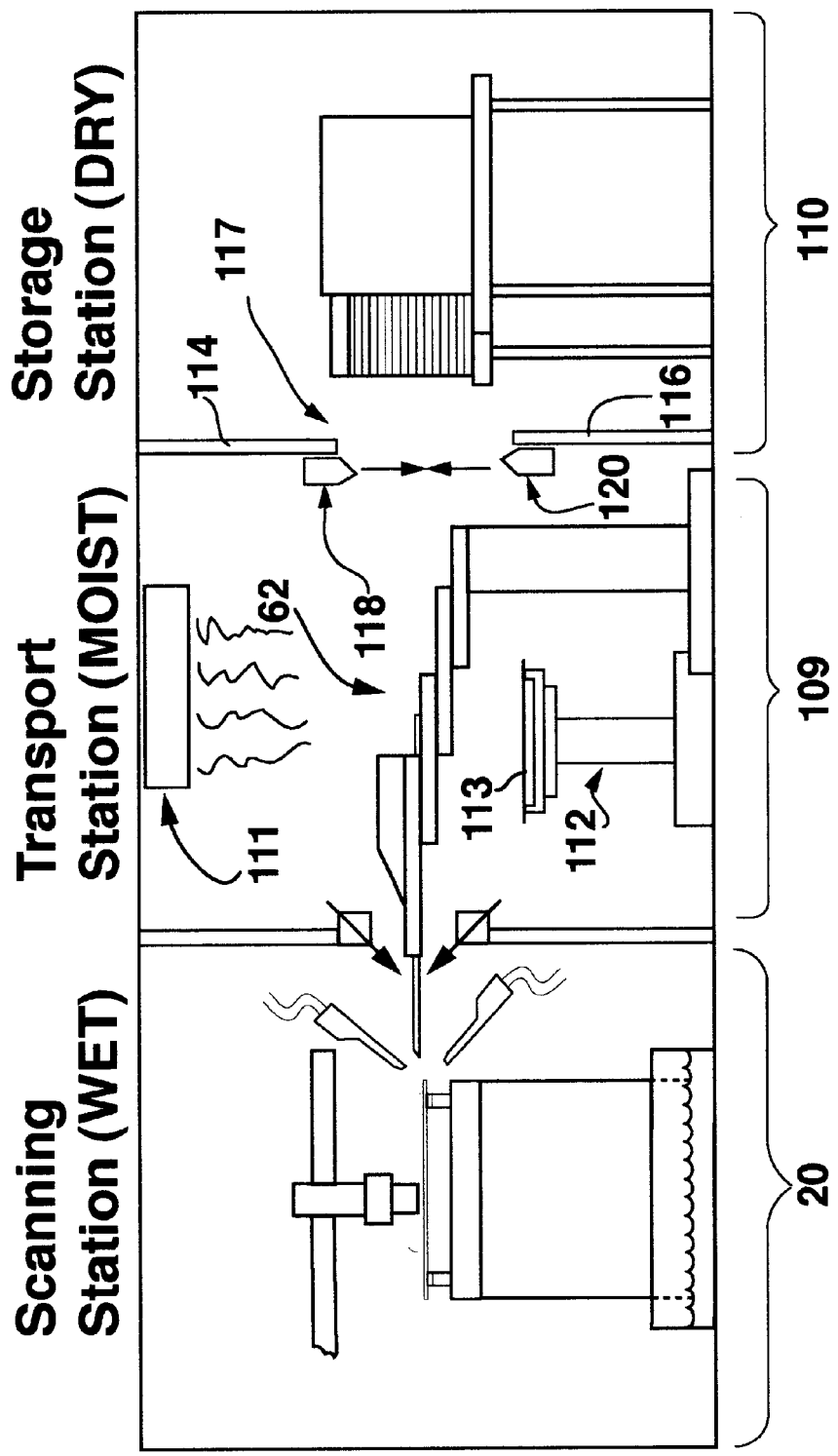
Figure 5:
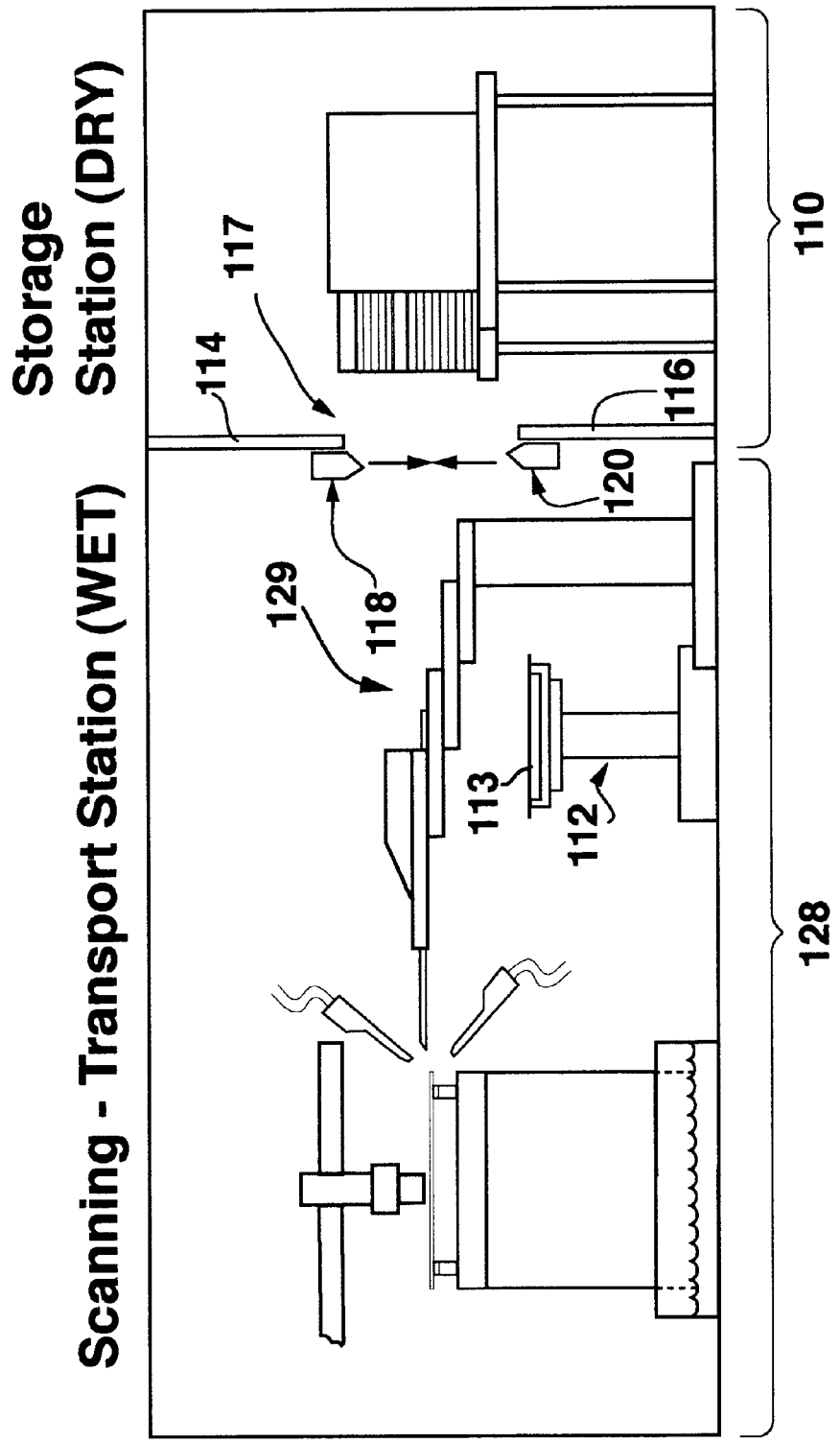

FIGS. 3–5 schematically illustrate different system layout configurations according to the invention to reduce the moisture content of AMI-inspected wafers before return to storage. In the layout of FIG. 3, a part-handling robot is located in a combined transport-storage station separated from a scanning station by a moisture barrier. In the layout of FIG. 4, a part-handling robot is located in a discrete transport station and moisture barriers are provided on each side of the transport station. In the FIG. 5 layout a parts-handling robot is wet-adapted and is located in the wet-environment AMI part scanning station.

Figure 1:
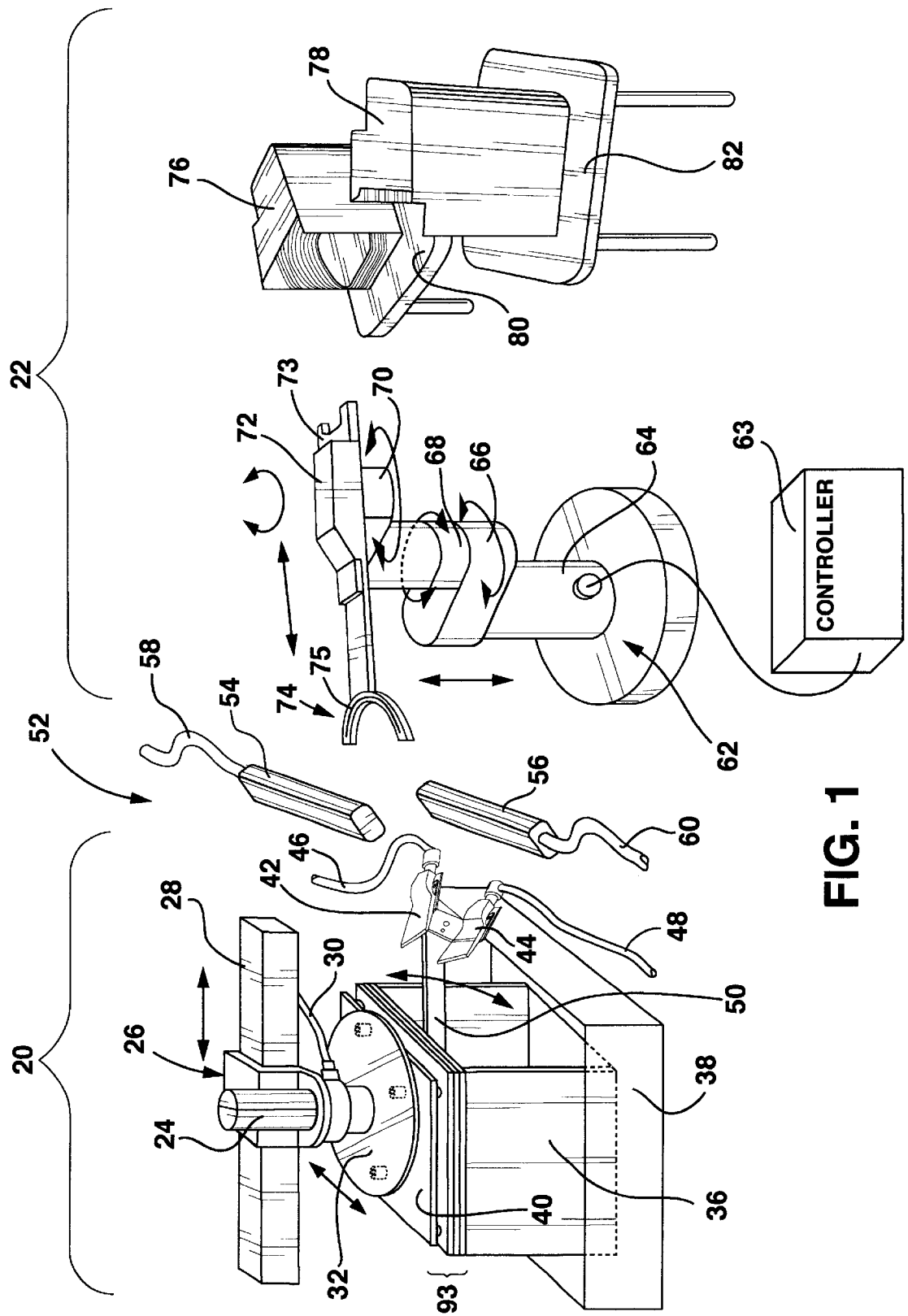
FIG. 1 is a schematic perspective view of a portion of the system of the invention for automated inspection of semiconductor wafers and other parts in an AMI inspection system.
Figure 2:
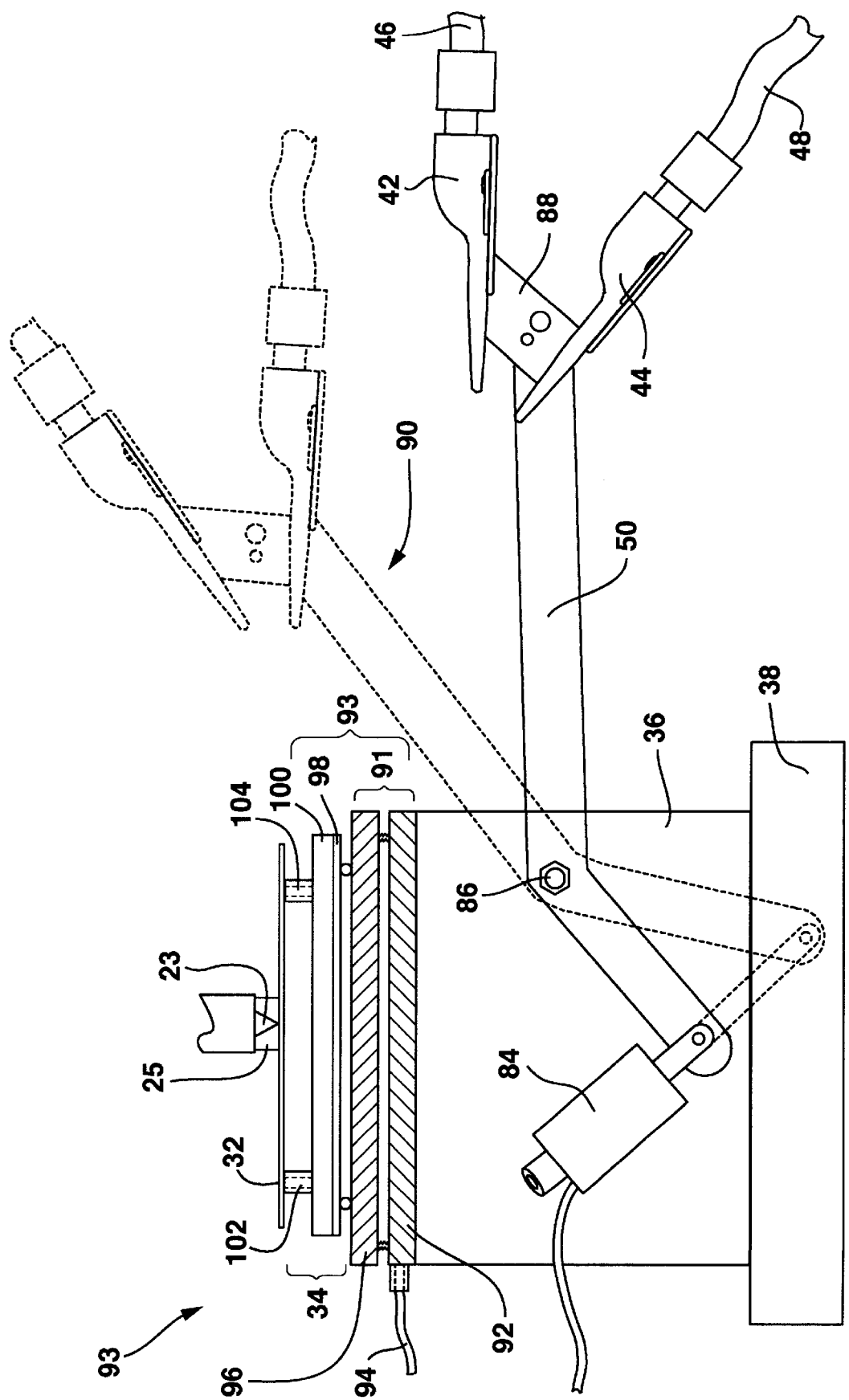
FIG. 2 is a sectional side elevation view of a part of a scanning station shown in FIG. 1.
Figure 6:
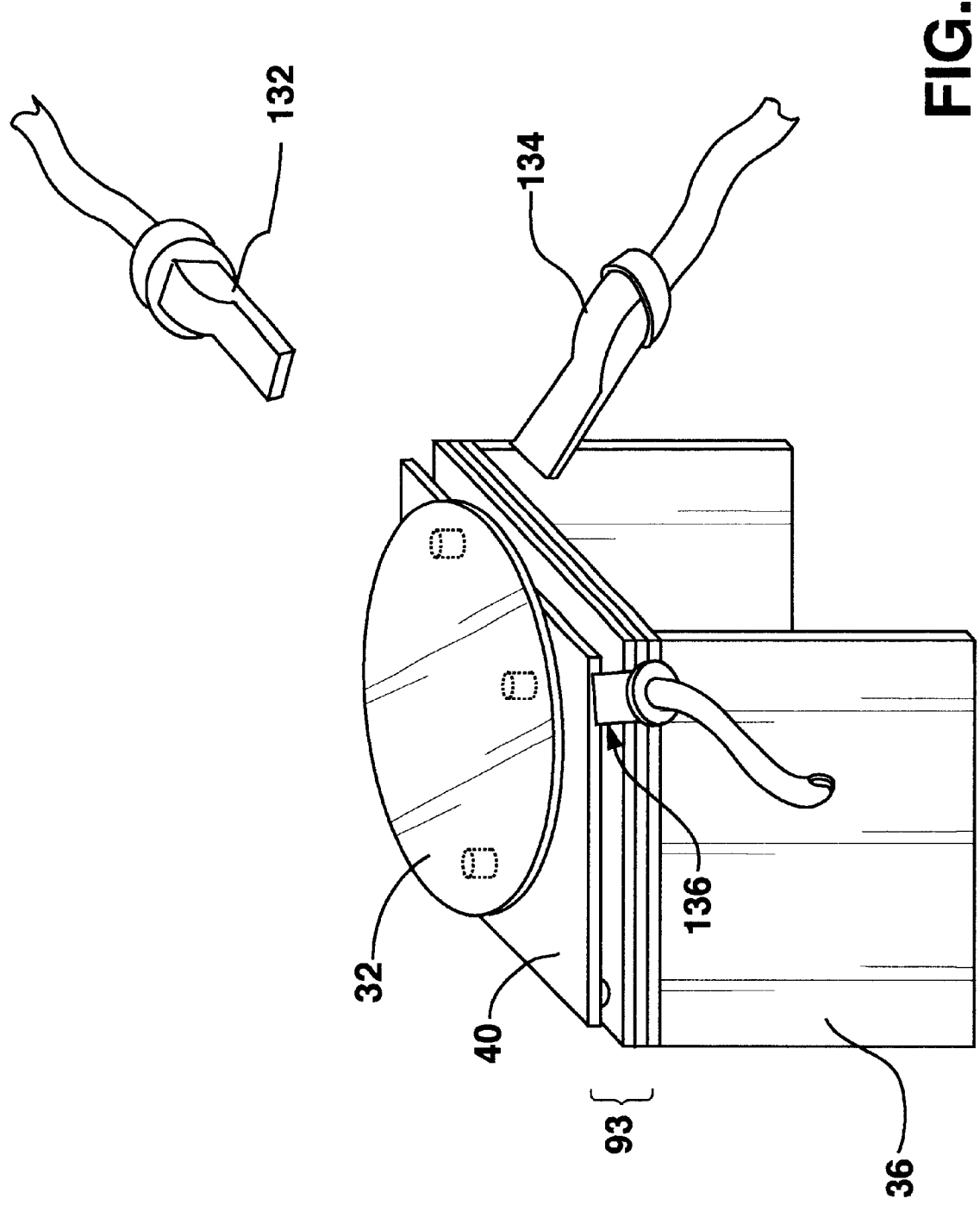
Figure 8:
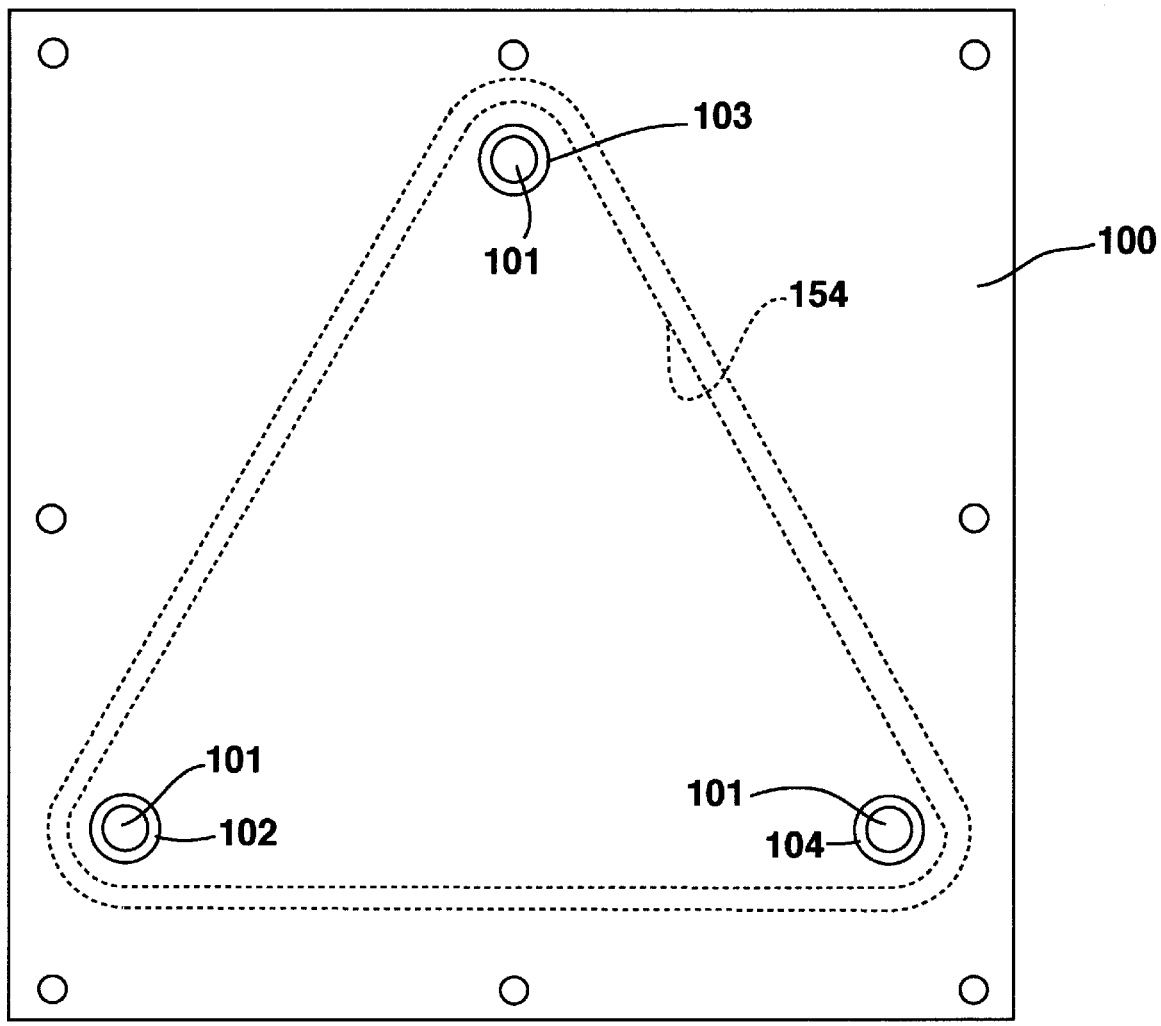
Figure 8A:
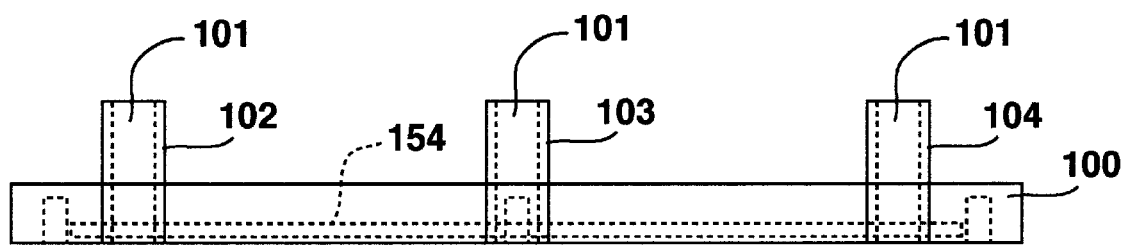

FIG. 6 is a schematic perspective view of an alternative preliminary dryer that may be employed instead of the dryer illustrated in FIGS. 1 and 2.

FIGS. 7, 7A, and 7B are perspective, side elevation, and exploded views of a part-retention stage illustrated in FIGS. 1–2 and constructed according to the principles of the present invention.

FIGS. 8, 8A, 9, 9A, 9B, 10, 10A, 11, 11A and 11B are orthographic projection views of the part-retention stage shown in FIGS. 7A and 7B.

Figure 12:
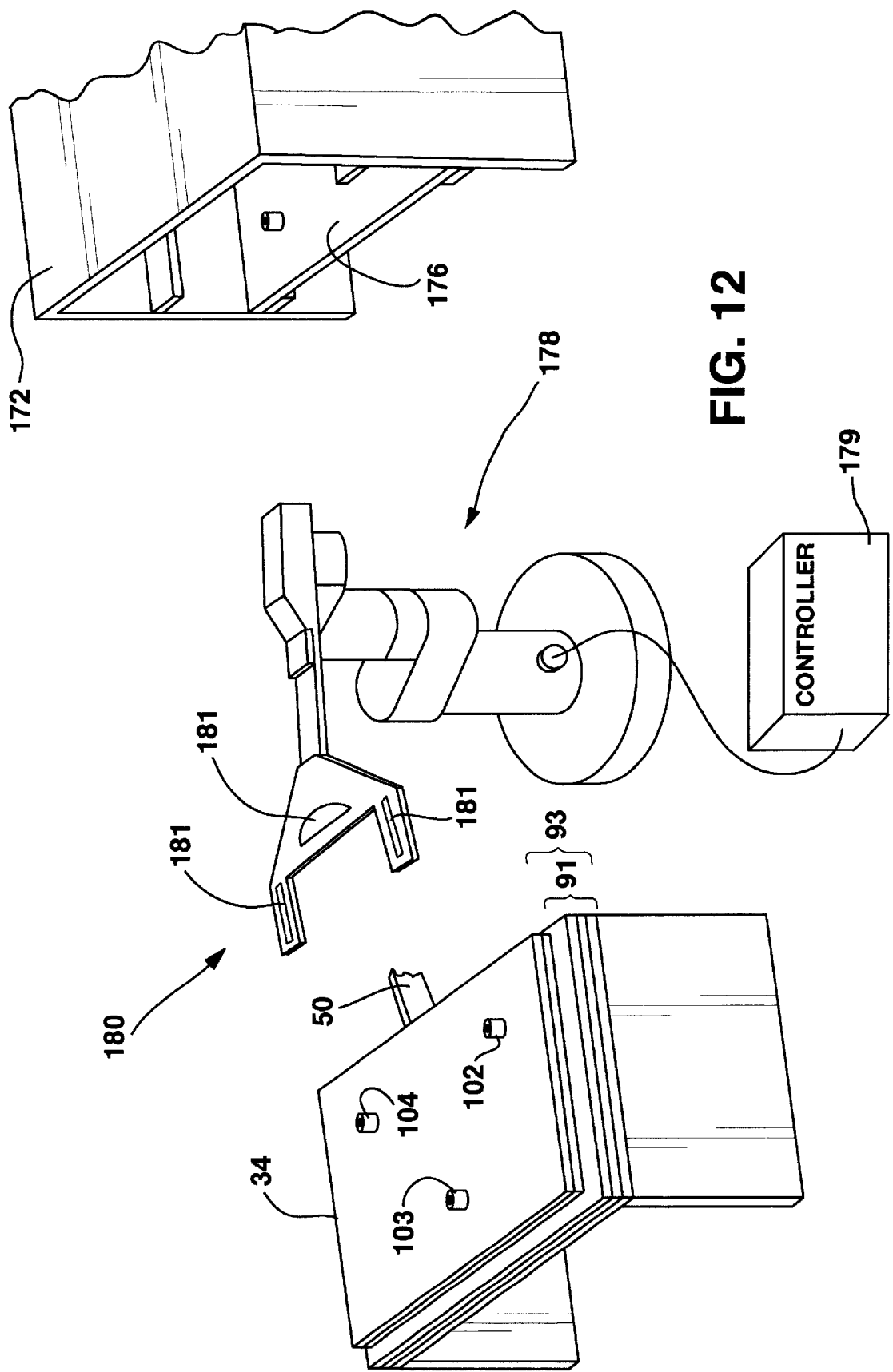

FIG. 12 is a schematic view of another portion of the system of the invention for automated inspection of semiconductor wafers in an AMI inspection system, illustrating robotic means for automatically interchanging vacuum chucks of the type detailed in FIGS. 7–11B.

FIG. 13 illustrates a buffer tank for softening the gas blast to the air knives depicted in FIGS. 1 and 6, for example.

FIG. 14 shows an alternative vacuum chuck main plate having provision for expediting drainage of coupling fluid.

FIGS. 15 and 16 are schematic illustrations of AMI system arrangements for automated inspection of parts which improve the robot duty cycle and throughput of the system.

DESCRIPTION OF THE PREFERRED EXECUTION OF THE INVENTION

The present invention is directed to an automated acoustic micro imaging ("AMI") inspection system and method that enables the automated inspection of various part sizes and configurations in the hostile wet-environment of an AMI system. As used herein "robot" means any programmable computer-controlled mechanical for performing prescribed motion functions. "Kinematic" or "kinematic mount" means any arrangement wherein two structures are separably coupled in such a way that relative movement therebetween is uniquely constrained, with the assistance of gravity or other force, in all six degrees of freedom, namely X-axis, Y-axis, Z-axis, roll, pitch and yaw.

A preferred apparatus and method of execution of the invention is illustrated in the Figures, in which like reference numerals in different figures indicate like structure and function. The elements of the depicted execution will be first listed and identified with brief descriptive annotations where necessary to enlighten one skilled in the art, followed by a concise description of the operation of the system. Finally, structure and method equivalents of the preferred execution will be described.

STRUCTURE OF THE PREFERRED EXECUTION

Reference Numeral Description

20 scanning station
22 part-storage station 23 ultrasonic beam 24 ultrasonic beam generator Sometimes termed a transducer.

25 coupling fluid

26 X–Y motion stage 28 support for X–Y motion stage 30 electrical cabling and coupling fluid hose for ultrasonic beam generator 32 part to be inspected Here shown as a semiconductor wafer.

34 vacuum chuck Accords with an aspect of the present invention.

36 scanning station legs 38 tank For retaining coupling fluid drainage.

42 preliminary dryer nozzle Directs a jet of air or other gas at robot-engaged lower surface of part 32 to be inspected when nozzle is elevated into its operative position. See FIG. 2, dotted-line position 90.

44 preliminary dryer nozzle Directs a jet of air or other gas at surface opposite to robot-engaged lower surface of part 32 when nozzle is elevated into its operative position. See FIG. 2, dotted-line position 90.

46 gas hose for nozzle 42

48 gas hose for nozzle 44

50 arm Supports nozzles 4 and 44.

52 moisture barrier 54 air knife 56 air knife Air knives 54, 56 create a moisture barrier which minimizes the migration of the wet-environment created in the scanning station during part inspection into the storage station 22 containing part-holding cassettes 76,78 and robot 62. Air knives 54 and 56 are preferably canted toward the scanning station 20 to improve the effectiveness of the moisture barrier 105.

58 air hose for air knife 54

60 air hose for air knife 56

62 robot For retrieving a part 32 from cassette 78, placing it on the vacuum chuck 34 in the scanning station 20, and returning same to the cassette 78 or the cassette 76 after it has been inspected. Robot 62 may, for example be of a type manufactured by Genmark, PRI Automation, and other suppliers.

63. controller For controlling the operation of the robot 62.

64 column 66 arm 68 arm 70 arm 72 head 73 presence detector Used to determine whether a part is in a particular cassette storage slot.

74 end effector 75 vacuum recess For gripping a part when end effector 74 is activated with a vacuum.

76 cassette For storing parts, here shown by way of example as wafers 32.

78 cassette For storing parts; may be used to store rejected parts which failed inspection.

80 support base 82 support base 84 pneumatic piston See FIG. 2. For pivoting nozzles 42,44 between an inoperative position (shown in unbroken lines in FIG. 2) and an operative position (shown in broken lines 90 in FIG. 2). In its operative position, nozzle 44 is directed to the undersurface of part 32 in the region where it is to be engaged by the end effector 74 of robot head 72. In its operative position nozzle 42 is directed at the opposed surface of part 32.

86 pivot bolt for arm 50

88 nozzle support bracket Attached to arm 50 and supports nozzles 42,44.

90 operative position of nozzles 42,44

91 stage base Kinematically supports vacuum chuck 34, as will be described.

92 base plate of stage base 93 See detail in FIGS. 7A, 7B, 11, 11A, and 11B.

93 part-retention stage Retains part 32 during AMI inspection and comprises stage base 91 and vacuum chuck 34.

94 vacuum line 96 kinematic plate Tilt-adjustably connected to base plate 92 by means of adjustment screws 146 working against the bias of springs 144. See FIGS. 7A and 7B.

98 vacuum chuck cover plate Has provisions for making a position-repeatable kinematic mating engagement with kinematic plate 96, as will be explained below. See FIGS. 7B, 9, 9A, and 9B.

100 vacuum chuck main plate Completes a vacuum conduit from an external vacuum source (not shown) through vacuum line 94, vacuum coupling 142 on base plate 92, channel 164 in base plate 92, coupling member 150, a vacuum recess 154 in main plate 100 to hollow cores 101 vacuum posts 102, 103, 104. See FIGS. 7A, 8, and 8A, for example. Details below. The vacuum chuck main plate 100 tends to collect a heavy accumulation of coupling fluid during the acoustic inspection operation which can aggravate the effort to dry the inspected part before return to storage. In accordance with an aspect of the invention, the plate 100 may be slightly domed or grooved or coated with a hydrophobic material to expedite drainage of coupling fluid collected on the chuck. FIG. 14 illustrates a vacuum chuck main plate which is slightly domed and provided with radial grooves.

101 hollow cores in vacuum posts 102, 103, and 104.

102 vacuum post 103 vacuum post 104 vacuum post The vacuum posts 102, 103, 104 have a height sufficient to: 1) elevate a supported part above coupling fluid drainage, 2) provide access for the end effector 74 of robot 62, and 3) provide a passageway for gas from gas nozzle 42 to clear moisture from the undersurface of a part to be gripped by the robot and puddling from the top surface of vacuum chuck main plate 100.

105 moisture barrier Function is to minimize moisture migration from the wet-environment scanning station 20 to the dry-environment part-storage station 22.

106 wall section Moisture impervious.

107 wall section Moisture impervious 109 transport station Contains robot 62 in the FIG. 4 layout. May also include auxiliary dryers to further reduce the moisture content on parts being returned to part-storage station 110. Examples here shown as including radiant energy dryer 111, and spin dryer 112 accessible to robot 62.

110 part-storage station 111 radiant energy dryer 112 spin dryer Shown as holding a part 113.

113 part 114 wall section Moisture impervious.

116 wall section Moisture impervious.

117 moisture barrier A tertiary moisture barrier to further insure that part returned to the part-storage station are adequately surface dry.

118 air knife 120 air knife 128 combined scanning-transport station In the FIG. 5 layout, the robot 129 is wet-adapted and resides in the wet-environment scanning station with the AMI system.

129 robot Wet-adapted. May be of a type manufactured by PRI Automation and other suppliers.

132 dryer nozzle 134 dryer nozzle 136 dryer nozzle FIG. 6 is an alternative to the preliminary dryer illustrated in FIGS. 1–2, comprising three permanently mounted nozzles 132, 134, 136 oriented such that at least a directional component of the gas stream is aimed away from the adjacent station to minimize the migration of moisture from the wet-environment AMI scanning station toward the part-storage station.

142 vacuum coupling 144 springs 146 adjustment screws 148a, 148b, 148c balls For use in effecting position-repeatable kinematic coupling of vacuum chuck 34 (through provisions on vacuum chuck cover plate 98) and stage base 91 (through provisions on kinematic plate 96). Balls 148a, 148b, 148 c are preferably adhered to kinematic plate 96. See FIGS. 7A, 7B, 9, 9A, 10 and 10A.

150 vacuum coupling member Anchored in opening 190 (FIG. 11A) in base plate 92 at the terminus of channel 164, passing through loose fit opening 184 in plate 96 (FIG. 10) to complete a vacuum conduit section between base plate 92 and cover plate 98. See FIG. 7A.

152 flexible cup Mates with and sealingly engages the periphery of opening 153 in cover plate 98 (FIG. 9) when vacuum chuck 34 is placed upon the stage base 91. Coupling member 150 thus functions to automatically complete a vacuum conduit from an external vacuum source to vacuum posts 102, 103, and 104 when vacuum chuck 34 is installed on base 91.

153 opening 154 vacuum recess 160 chamfered hole Part of kinematic mount arrangement, engaging ball 148a.

162 chamfered slot Part of kinematic mount arrangement, engaging ball 148b.

163 recessed flat Part of kinematic mount arrangement, engaging ball 148c. The chamfered hole 160 engages ball 148a, the chamfered slot 162 engages ball 148b, and the recessed flat 163 engages ball 148c to constrain all degrees of freedom of the chuck 34 relative to the base 91, thus defining a position-repeatable kinematic mount of the vacuum chuck 34 upon the base 91.

Figure 10:
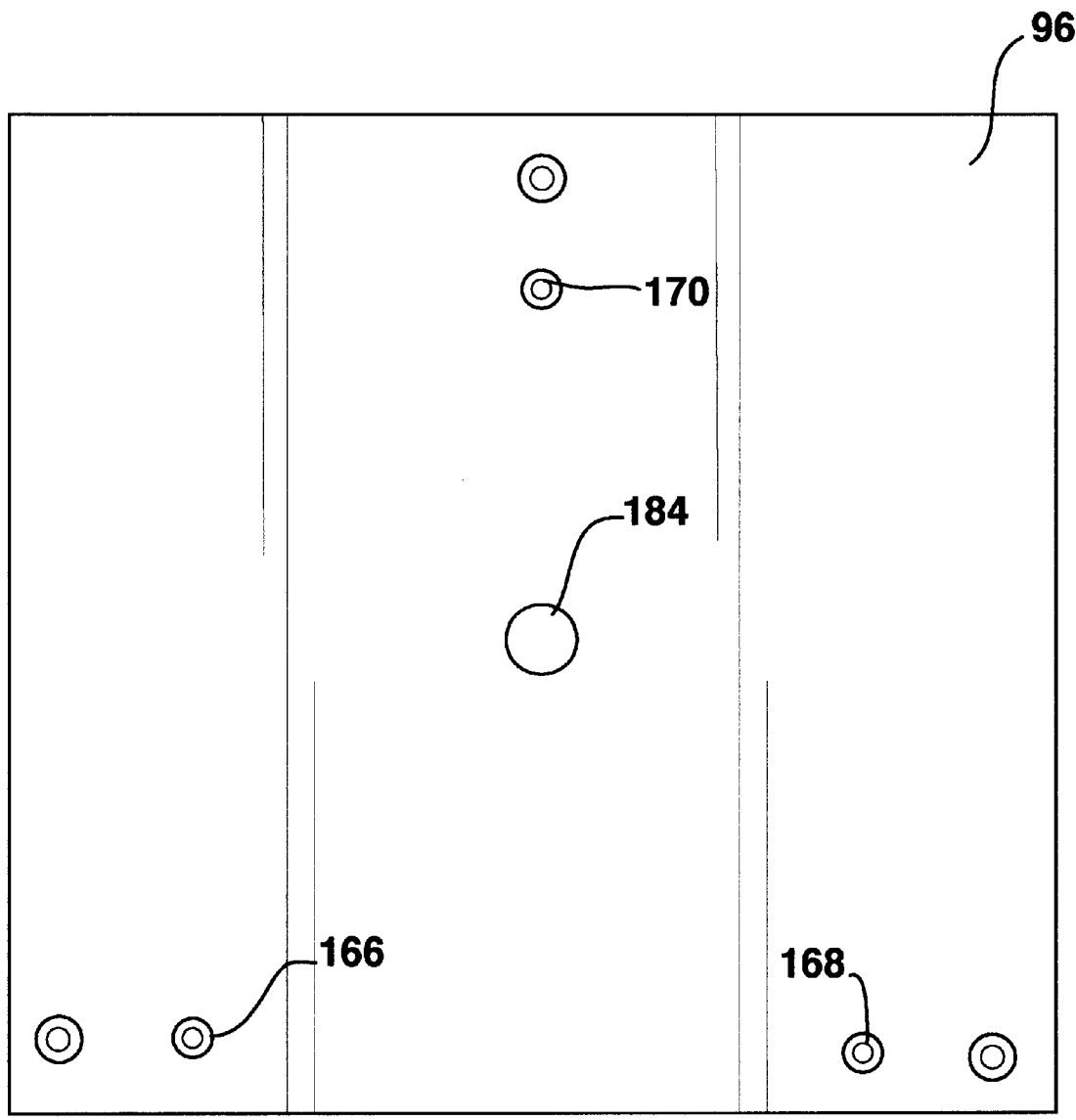
Figure 10A:
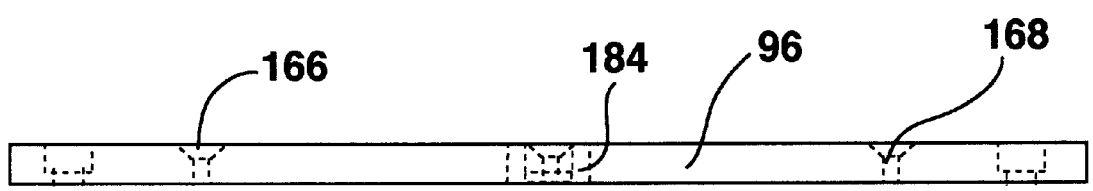

164 channel or bore 166 chamfered hole For receiving ball 148a (FIG. 10).

168 chamfered hole For receiving ball 148b (FIG. 10).

170 chamfered hole For receiving ball 148c (FIG. 10).

172 vacuum chuck storage rack See FIG. 12.

176 vacuum chuck Vacuum chuck 176 may have a different size and/or configuration than vacuum chuck 34, but must have a kinematic mount arrangement which is similar thereto and compatible with that of kinematic plate 96 comprising part of stage base 91.

178 robot For interchanging vacuum chucks 34, 176. May be similar to robot 62 but more robust.

179 controller For controlling the robot 178.

180 magnetic end effector 181 vacuum recesses The function of robot 178 is to automatically retrieve vacuum chuck 34 from the part-retention stage 93 and substitute a predetermined alternate vacuum chuck such as shown at 176. The end effector 180 lifts and vacuum grips the vacuum chucks during the chuck interchange process in a manner similar to operation of robot 62.

190 buffer tank 192 inlet line 194 gas pump 196 outlet line 200 acoustic micro imaging system 202 acoustic micro imaging system 204 X–Y scanning transducer 205 robot 206 dryer 208 dryer 210 storage station 212 storage station 213 scanning transducer 214 part-retention stage 216 part-retention stage.

OPERATION

The preferred system which has been described executes a method for automated AMI inspection of semiconductor wafers or other parts stored in a dry-environment storage station. The various aspects of the present invention for which protection is sought by this patent are described precisely in the appended claims. The preferred method and system illustrated and described above, in broad review, comprises robotically retrieving a dry part from the storage station and placing it on a vacuum chuck in a part-retention stage in an AMI system station. The part is probed with an ultrasonic beam generated by a beam generator in the presence of a coupling fluid such as water. The coupling fluid undesirably creates a wet scanning environment that is hostile to robotic handling and post inspection storage of the part. In accordance with an aspect of the invention, the vacuum chuck elevates the part above the coupling fluid drainage.

To facilitate robotic retrieval of the part from the wet-environment scanning station, the part is subjected to a preliminary drying operation which may, for example, employ gas jets directed on the surface or surfaces to be engaged by the involved robot. The part is then robotically retrieved from the vacuum chuck and returned to the dry-environment storage station.

Because of the high state of wetness of, and space restrictions in, the scanning station, the preliminary drying operation may not sufficiently dry the part before it is returned to storage. To enhance the state of dryness of the part, a moisture barrier is preferably provided between the scanning station and the storage station. The moisture barrier may comprise any of a variety of means such as flexible lips or strands, heat, or forced gas. To further enhance the state of dryness of a part before re-storage, additional dryers may be employed, including a spin station, radiant heat, a vacuum oven or the like.

In order to further automate the process, another aspect of the present invention comprises robotically interchanging vacuum chucks to enable automated handing of parts of different sizes and configurations. In accordance with an aspect of the present invention the novel vacuum chuck is capable of quick-exchange, position-repeat, automatic vacuum restoration, and tilt adjustment.

A part, which may be different from a part inspected employing the first vacuum chuck, is retrieved from storage, and placed upon the exchanged vacuum chuck where it is inspected, dried preliminary to robotic pickup, and robotically returned to storage after subsequent moisture removal, if and as needed.

Thus, by the present invention, for the first time semiconductor wafers and other parts of differing sizes and configurations may be automatically inspected and handled in the hostile wet-environment of an AMI system without the need for manual intervention to change parts or part-retention equipment.

OTHER EQUIVALENTS OF THE PREFERRED EMBODIMENT

Structures and methods that may be employed to implement the principles of the invention, other than those identified above, will now be described. Whereas semiconductor wafers are illustrated as the type of parts handled by the present system, other parts such as flat panels displays, ceramic plates, PC boards and trays of parts may be handled. The storage means is shown as wafer cassettes 76,78, however, other part-storage containers such as flat panel display cassettes, part magazines, etc. may be employed.

A great variety of robotic devices may be employed for transporting parts to and from the scanning station. As noted, if situated in the scanning station the robot 62 is preferably wet-adapted, such as the "WETBOT" manufactured by PRI Automation. If located outside of the wet-environment scanning station, it is not necessary to employ a robot which has been provided with wet-condition resistance.

In the scanning station, an AMI system has been illustrated which is capable of X–Y scanning motion, however, another arrangement is contemplated wherein the beam generator moves in one dimension only and the part is moved in the orthogonal dimension. The part-retention is illustrated as being accomplished by a vacuum chuck, however, aspects of the invention could be implemented with part-retention by other than a vacuum chuck. In the preferred execution of the invention, a vacuum chuck is employed using three vacuum posts to elevate the inspected part above the coupling fluid drainage, however this objective could be accomplished in other ways. Various arrangements other than that shown could be employed for forming a vacuum conduit from an external vacuum source to the part being retained.

The kinematic mount aspect of the invention could be accomplished in a variety of ways other than the illustrated 4-point arrangement employing three balls mating with a countersunk hole, a groove and a flat. Various means other than a coupling member as shown at 150 could be employed for completing the described vacuum conduit.

The moisture barrier 52 could be constructed using instrumentalities other than a pair of air knives. The illustrated arrangement of a pair of air knives mounted on a pivoted arm has the advantage of moving the preliminary drying gases in close proximity to the part surface to be engaged by the robot while directing the gas jets away from the part-storage station. These objectives can be accomplished using other means for moving the dryers in and out of such efficacious operating position. And, as noted, dryers other than one or more air knives may be employed.

Commercially available air knives of the type described have a tendency to start with a sharp blast of air which has been found to dislodge the part inspected and dispatch large amounts of moisture where it is not wanted. To overcome this too-sudden volume ramp-up, a buffer tank may be inserted in the line 192 from a gas pump 194, as shown in FIG. 13. With this feature, when the air knife pump 194 is activated, the sudden blast of gas it creates first compresses gas in the tank 190 which is then released less suddenly into the outlet gas line 196. The volume of gas discharge from the knife thus builds up more gradually than would be the case without the buffer tank. The discharge volume versus time waveform can be controlled by the capacity of the tank and the diameter and length of the lines 192 and 196.

The present invention contemplates a number of ways to improve the duty cycle of the robot(s) employed. FIG. 15 schematically illustrate an arrangement wherein a plurality of wet-environment acoustic micro imaging systems 200, 202, each having a part-retention stage, are serviced by a single X–Y scanning transducer 204 which moves back and forth between the two stages 200, 202. A single robot 205 is active in cycling parts between storage stations 210, 212, micro imaging systems 200, 202, dryers 206, 208 and back to storage stations 210, 212.

An arrangement shown in FIGS. 16 differs from the FIG. 15 arrangement in that the transducer 213 does not move, but has an X–Y span great enough to encompass two part-retention stages 214, 216.

While particular embodiments of the present invention have been shown and described, it will be obvious to those skilled in the art that other changes and modifications may be made without departing from the invention in its broader aspects. The appended claims are intended to cover all such changes and modifications that fall within the true spirit and scope of the invention. The matter set forth in the foregoing description and accompanying drawings is offered by way of illustration only and not as a limitation on the scope of the invention.

What is claimed is:

1. An automated acoustic micro imaging system, comprising:
   a part-storage station favoring a dry environment;
   a part-transport robot favoring a non-wet part-handling environment; and
   a wet-environment inspection station including:
      an ultrasonic beam generator,
      a beam-coupling fluid,
      a part-retention stage, and
      a preliminary dryer for at least partially removing coupling fluid from a part which has been inspected by an ultrasonic beam from the beam generator in a coupling fluid environment, but before being picked up by the robot, thereby facilitating the robot pickup and reducing the amount of coupling fluid carried to the part-storage station by the robot.

2. The system defined by claim 1 wherein said preliminary dryer includes a gas jet directed at a first surface of a part to be engaged by said robot.

3. The system defined by claim 2 wherein said preliminary dryer includes a second gas jet directed at a second surface of the part which is opposed to said first surface.

4. The apparatus defined by claim 2 including a gas pump supplying gas under pressure to said gas jet through a line which includes a buffer tank for softening the gas blast when the pump is activated.

5. The system defined by claim 1 wherein said preliminary dryer is adapted to be moved between an inoperative position and an operative position.

6. The system defined by claim 5 wherein said dryer comprises a gas jet aimed away from said part-storage station when said dryer is in said operative position.

7. The system defined by claim 1 wherein said dryer includes at least one permanently mounted gas jet aimed at said part in a direction having a component oriented away from said part-storage station.

8. The apparatus defined by claim 7 including a gas pump supplying gas under pressure to said gas jet through a line which includes a buffer tank for softening the gas blast when the pump is activated.

9. The system defined by claim 1 wherein said preliminary dryer comprises a spin dryer.

10. The system defined by claim 1 wherein said system includes a secondary dryer for enhancing the dryness of the part before being returned to the part-storage station.

11. An automated acoustic micro imaging system, comprising:
   a part-storage station favoring a dry environment;
   a wet-environment inspection station including:
      an ultrasonic beam generator,
      a coupling fluid in which parts are inspected, and
      a part-retention stage;
   a part-transport station located between said part-storage station and said inspection station and including a part-handling robot; and
   a moisture barrier located between said wet-environment inspection station and said part-transport station.

12. The system defined by claim 11 wherein said moisture barrier comprises a gas curtain effective to pass a robot arm while impeding the migration of moisture from said inspection station to said part-transport station.

13. The system defined by claim 12 wherein said gas curtain is formed by a pair of opposed gas knives, said gas knives being canted toward said inspection station to improve the moisture retention effectiveness of said knives.

14. The system defined by claim 11 including a second moisture barrier located between said transport station and said storage station.

15. The system defined by claim 14 wherein said second moisture barrier comprises a gas curtain effective to pass a robot arm while impeding the migration of moisture from said part-transport station to said part-storage station.

16. An automated acoustic micro imaging system, comprising:
   a part-storage station favoring a dry environment;
   a part-transport robot favoring a non-wet part-handling environment;
   a wet-environment inspection station including:
      an ultrasonic beam generator,
      a beam-coupling fluid,
      a part-retention stage, and
      a preliminary dryer for at least partially removing coupling fluid from a part which has been probed by an ultrasonic beam from the beam generator in a coupling fluid environment, but before being picked up by the robot, thereby facilitating the robot pickup and reducing the amount of coupling fluid carried to the part-storage station by the robot; and
   a moisture barrier located between said wet-environment inspection station and said part-storage station favoring a dry environment.

17. The system defined by claim 16 wherein said preliminary dryer includes a gas jet directed at a first surface of a part to be engaged by said robot.

18. The system defined by claim 17 wherein said preliminary dryer includes a second gas jet directed at a second surface of the part which is opposed to said first surface.

19. The apparatus defined by claim 17 including a gas pump supplying gas under pressure to said gas jet through a line which includes a buffer tank for softening the gas blast when the pump is activated.

20. The system defined by claim 16 wherein said preliminary dryer is adapted to be moved between an inoperative position and an operative position.

21. The system defined by claim 20 wherein said dryer comprises a gas jet aimed away from said part-storage station when said dryer is in said operative position.

22. The system defined by claim 16 wherein said dryer includes at least one permanently mounted gas jet aimed at said part in a direction having a component oriented away from said part-storage station.

23. The system defined by claim 16 wherein said robot favors a dry environment and is located in said part-storage station.

24. The system defined by claim 16 wherein said robot is wet-adapted and is located in said wet-environment inspection station.

25. The system defined by claim 16 where said system includes a part-transport station between said inspection station and said part-storage station which contains said robot, and wherein said moisture barrier is located between said inspection station and said part-transport station.

26. The system defined by claim 25 wherein said system includes a second moisture barrier between said part-transport station and said part-storage station.

27. The system defined by claim 16 where said system includes a part-transport station between said inspection station and said part-storage station which contains said robot, and wherein said part-transport station includes a dryer.

28. An automated acoustic micro imaging system, comprising:
   a part-storage station favoring a dry environment;
   a part-transport robot;
   a wet-environment scanning station including:
      an ultrasonic beam generator,
      a coupling fluid in which parts are inspected, and
      a part-retention stage; and
   a moisture barrier located between said wet-environment inspection station and said part-storage station favoring a dry environment.

29. The system defined by claim 28 wherein said robot favors a dry environment and is located in said part-storage station.

30. The system defined by claim 28 wherein said robot is wet-adapted and is located in said wet-environment inspection station.

31. The system defined by claim 28 where said system includes a part-transport station between said inspection station and said part-storage station which contains said robot, and wherein said moisture barrier is located between said inspection station and said part-transport station.

32. The system defined by claim 31 wherein said system includes a second moisture barrier between said part-transport station and said part-storage station.

33. The system defined by claim 28 where said system includes a part-transport station between said inspection station and said part-storage station which contains said robot, and wherein said part-transport station includes a dryer.

34. An acoustic micro imaging system, comprising:
a wet-environment inspection station including:
an ultrasonic beam generator,
a beam-coupling fluid,
a part-retention stage, and
a part dryer for at least partially removing coupling fluid from a part which has been inspected by an ultrasonic beam from the beam generator in a coupling fluid environment.

35. The system defined by claim 34 wherein said dryer includes a gas jet directed at a fist surface of a part.

36. The system defined by claim 35 wherein said dryer includes a second gas jet directed at a second surface of the part which is opposed to said first surface.

37. The system defined by claim 34 wherein said dryer is adapted to be moved between an inoperative position while said part is being inspected and an operative position after the part has been inspected.

38. The system defined by claim 34 wherein said dryer includes at least one permanently mounted gas jet aimed at said part in a direction having a component oriented away from said part-storage station.

39. The system defined by claim 34 wherein said preliminary dryer comprises a spin dryer.

40. An automated acoustic micro imaging system, comprising:
an inspection station including an ultrasonic beam generator and a part-retention stage including a kinematically mounted part-retaining chuck; and
robot means for picking parts to be inspected, depositing them at said part-retention stage, and removing them from said part-retention stage after they have been inspected in said inspection station, and for automatically interchanging part-retaining chucks.

41. The apparatus defined by claim 40 wherein said inspection station has a coupling fluid environment, and wherein said apparatus includes a preliminary dryer for at least partially removing coupling fluid from a part which has been inspected, but before being picked up by the robot means, thereby facilitating the pickup by the robot means and reducing the amount of moisture carried by the part away from the inspection station.

42. The apparatus defined by claim 40 wherein said part-retention stage includes a stage base adapted to be connected to a vacuum source, and wherein said part-retaining chuck is a vacuum chuck supported on said stage base in a quick-change, position-repeatable kinematic mount arrangement, said stage base and said vacuum chuck being configured such that a sealed vacuum conduit is formed between a vacuum source connected to said stage base and a part placed upon said vacuum chuck, whereby kinematic positioning accuracy is retained and vacuum integrity is preserved when said vacuum chuck is replaced on said stage base by another vacuum chuck having a similarly constructed kinematic mount arrangement.

43. An acoustic micro imaging system, comprising:
an ultrasonic beam generator; and
a part-retention stage for supporting a part as it is being inspected by an ultrasonic beam from the beam generator, said part-retention stage comprising:
a stage base adapted to be connected to a vacuum source, and
a part-retaining vacuum chuck supported on said stage base in a quick-change, position-repeatable kinematic mount arrangement, said stage base and said vacuum chuck being constructed such that a sealed vacuum conduit is formed between a vacuum source connected to said stage base and a part placed upon said vacuum chuck, whereby kinematic positioning accuracy is retained and vacuum integrity is preserved when said vacuum chuck is replaced on said stage base by another vacuum chuck having a similarly constructed kinematic mount arrangement.

44. The apparatus defined by claim 43 wherein said sealed vacuum conduit is formed automatically when a vacuum chuck is placed upon said stage base.

45. The apparatus defined by claim 43 wherein said vacuum conduit includes a hollow coupler anchored at one end in said stage base and having at its opposed end a flexible cup sealingly engaging the periphery of a vacuum conduit opening in said vacuum chuck.

46. The apparatus defined by claim 44 wherein said stage base includes a base plate and a kinematic plate tilt-adjustably connected to said base plate and kinematically couplable to said vacuum chuck.

47. The apparatus defined by claim 46 wherein said vacuum conduit includes a hollow coupler anchored at one end in said base plate and having at its opposed end a flexible cup sealingly engaging the periphery of a vacuum conduit opening in said vacuum chuck.

48. The apparatus defined by claim 43 wherein said vacuum chuck includes a plurality of hollow part-supporting posts forming part of said vacuum conduit, said posts having a predetermined common height effective to elevate a inspected part above coupling fluid collected on said vacuum chuck during a part scanning operation.

49. The apparatus defined by claim 48 wherein said vacuum chuck includes means for expediting drainage of said coupling fluid collected on said vacuum chuck.

50. An automated acoustic micro imaging system, comprising:
an ultrasonic beam generator; and
a part-retention stage for supporting a part as it is being inspected by an ultrasonic beam from the beam generator, said part-retention stage comprising:
a stage base, and
a part-retaining chuck supported on said stage base in a quick-change, position-repeatable kinematic mount arrangement; and
a robot for automatically replacing said chuck with a second chuck having a similarly constructed kinematic mount arrangement.

51. An automated acoustic micro imaging system, comprising:
an ultrasonic beam generator; and
a part-retention stage for supporting a part as it is being inspected by an ultrasonic beam from the beam generator, said part-retention stage comprising:
a stage base adapted to be connected to a vacuum source, and
a part-retaining vacuum chuck supported on said stage base in a quick-change, position-repeatable kinematic mount arrangement; and
a robot for automatically replacing said vacuum chuck with a second vacuum chuck having a similarly constructed kinematic mount arrangement, said stage base and said vacuum chuck being constructed such that a sealed vacuum conduit is formed between a vacuum source connected to said stage base and a part placed upon said vacuum chuck, whereby kinematic positioning accuracy is retained and vacuum integrity is automatically preserved between said stage base and said vacuum chuck when said robot replaces said vacuum chuck with another vacuum chuck having a similarly constructed kinematic mount arrangement.

52. The apparatus defined by claim 51 wherein said sealed vacuum conduit is formed automatically when a vacuum chuck is placed upon said stage base.

53. The apparatus defined by claim 52 wherein said vacuum conduit includes a hollow coupler anchored at one end in said stage base and having at its opposed end a flexible cup sealingly engaging the periphery of a vacuum conduit opening in said vacuum chuck.

54. The apparatus defined by claim 51 wherein said stage base includes a base plate and a kinematic plate tilt-adjustably connected to said base plate and kinematically coupled to said vacuum chuck.

55. The apparatus defined by claim 54 wherein said vacuum conduit includes a hollow coupler anchored at one end in said base plate and having at its opposed end a flexible cup sealingly engaging the periphery of a vacuum conduit opening in said vacuum chuck.

56. The apparatus defined by claim 54 wherein said vacuum chuck includes a plurality of hollow part-supporting posts forming part of said vacuum conduit, said posts having a predetermined common height effective to elevate a inspected part above coupling fluid drainage produced during a part scanning operation.

57. The apparatus defined by claim 51 including a second robot for automatically interchanging parts to be inspected between a part-storage station and said part-retention stage.

58. The apparatus defined by claim 56 wherein said parts are inspected in a coupling fluid environment, and wherein said system includes a preliminary dryer for at least partially drying said parts before being retrieved by said second robot for return to said storage station.

59. The apparatus defined by claim 58 including a secondary dryer to enhance the dryness of said parts before they are returned to said storage station.

60. A method for automated inspection of semiconductor wafers or other parts stored in a dry-environment storage station, comprising:

robotically retrieving a dry part from said storage station and placing it in a part-retention stage in an inspection station;

inspecting the part with an ultrasonic beam in the presence of a beam-coupling fluid, thereby undesirably creating a wet scanning environment hostile to robotic handling;

at least partially drying the part preliminary to robotic pickup; and robotically retrieving the part from the inspection station and returning it to the dry environment storage station, the drying of the part preliminary to robotic pickup serving to facilitate pickup of the part by the robot and to reduce the amount of coupling fluid carried to the storage station.

61. A method for automated inspection of semiconductor wafers or other parts stored in a dry-environment storage station, comprising:

robotically retrieving a dry part from said storage station and placing it in a part-retention stage in an inspection station;

inspecting the part with an ultrasonic beam in the presence of a beam-coupling fluid, thereby undesirably creating a wet scanning environment hostile to robotic handling;

at least partially drying the part preliminary to robotic pickup;

robotically retrieving the part from the inspection station and returning it to the dry environment storage station, the drying of the part preliminary to robotic pickup serving to facilitate pickup of the part by the robot and to reduce the amount of coupling fluid carried to the storage station; and providing secondary drying of a part being returned to the storage station to enhance the drying of the part effected by said preliminary drying operation.

62. A method for automated inspection of semiconductor wafers or other parts, comprising:

robotically retrieving a first part from storage and placing it on a first part-retaining chuck in a part-retention stage in an inspection station;

probing the part with an ultrasonic beam;

robotically retrieving the first part from the inspection station and returning it to storage;

robotically substituting a second part-retaining chuck for said first part-retaining chuck;

robotically retrieving a second part from storage and placing it on said second chuck;

probing the second part with an ultrasonic beam; and robotically retrieving the second part from the inspection station and returning it to storage.

63. The method defined by claim 62 wherein said inspection is conducted in the environment of a coupling fluid, and wherein before said parts are retrieved from the inspection station they are at least partially dried.

64. The method defined by claim 62 where said chucks are vacuum chucks which are kinematically retained on said part-retention stage, and wherein vacuum integrity is automatically restored after the interchange of vacuum chucks.

65. A method for automated inspection of semiconductor wafers or other parts stored in a dry-environment storage station, comprising:

robotically retrieving a dry part from said storage station and placing it in a first vacuum chuck in a part-retention stage in an inspection station;

probing the part with an ultrasonic beam in the presence of a beam-coupling fluid, thereby undesirably creating a wet scanning environment hostile to robotic handling;

preliminarily drying the first part;

robotically retrieving the part from the first vacuum chuck and returning it to the dry environment storage station;

robotically substituting a second vacuum chuck for said first vacuum chuck, said second vacuum chuck being configured to hold a second part differently configured from said first part;

robotically retrieving the second part from said storage station and placing it on said second vacuum chuck;

probing the second part with an ultrasonic beam in the presence of a beam-coupling fluid;

drying the second part preliminary to robotic pickup;

robotically retrieving the second part from the second vacuum chuck and returning it to said storage station;

the drying of the parts preliminary to robotic pickup serving to facilitate pickup of the parts by the robot and to reduce the amount of coupling fluid carried thereby to the storage station; and providing secondary drying of the first and second parts being returned to the storage station to enhance the drying of the parts effected by said preliminary drying operations.

66. The apparatus defined by claim 35 including a gas pump supplying gas under pressure to said gas jet through a line which includes a buffer tank for softening the gas blast when the pump is activated.

67. A method for automated inspection of semiconductor wafers or other parts, comprising:

providing a plurality of wet-environment acoustic micro imaging systems, each having a part-retention stage; and robotically moving parts between one or more part-storage stations and at least one of said plurality of acoustic micro imaging systems for inspection, said plurality of micro imaging systems being serviced by the same acoustic scanning transducer.

68. The method defined by claim 67 wherein the acoustic scanning transducer moves between spatially separated part-retention stages.

69. The method defined by claim 67 wherein the acoustic scanning transducer has an X–Y scan which encompasses a plurality of part-retention stages.

70. A method for automated inspection of semiconductor wafers or other parts, comprising:

providing one or more dryers and at least one wet-environment acoustic micro imaging system having a part-retention stage; and robotically moving parts in a cycle including a part-storage station, an acoustic micro imaging system for inspection, a dryer and a storage station.

71. The method defined by claim 70 including a plurality of micro imaging systems, said plurality of micro imaging systems being serviced by the same acoustic scanning transducer.

72. The method defined by claim 71 including spatially separated part-retention stages, the acoustic scanning transducer moving between said spatially separated part-retention stages.

73. The method defined by claim 72 wherein the acoustic scanning transducer has an X–Y scan which encompasses said spatially separated part-retention stages.

74. An acoustic micro imaging system, comprising:

a wet-environment scanning station including:
an ultrasonic beam generator,
a beam-coupling fluid, and
a part-retention stage having an upwardly facing surface which is undesirably prone to become laden with coupling fluid during inspection of a part, said surface being configured and arranged to expedite drainage of coupling fluid therefrom.

75. The apparatus defined by claim 74 wherein said surface is convexly curved.

76. The apparatus defined by claim 74 wherein said surface has drainage grooves.

* * * * *